United States Patent [19]

Robertson

[11] Patent Number: 5,513,985
[45] Date of Patent: * May 7, 1996

[54] DENTAL IMPRESSION TRAY

[76] Inventor: Walter H. Robertson, 1669 Palo Santo Dr., Campbell, Calif. 95008

[*] Notice: The portion of the term of this patent subsequent to May 31, 2011, has been disclaimed.

[21] Appl. No.: 214,436

[22] Filed: Mar. 18, 1994

[51] Int. Cl.⁶ ............................................. A61C 9/00
[52] U.S. Cl. ................................... 433/38; 433/37
[58] Field of Search ............................ 433/37, 38, 41, 433/42, 43, 44, 71, 214

[56] References Cited

U.S. PATENT DOCUMENTS

| | | | |
|---|---|---|---|
| 1,652,910 | 12/1927 | Psayla | 433/45 |
| 1,979,493 | 11/1934 | Salvio | 433/38 |
| 4,445,854 | 5/1984 | Bekey et al. | 433/37 |
| 4,689,010 | 8/1987 | Wolfe | 433/38 |
| 5,316,474 | 5/1994 | Robertson | 433/38 |

Primary Examiner—Cary E. O'Connor
Attorney, Agent, or Firm—Roger A. Marrs

[57] ABSTRACT

A dental impression tray is disclosed herein having a pair of spaced-apart arcuate walls having a common radial center and wherein the opposing wall surfaces define a work area for holding a quantity of dental impression material. A thin plastic embedded fibrous membrane or sheet or a non-woven fabric material extends across the work area having its opposite edges attached to the walls and separating the walls into upper and lower wall sections. One end of the walls may or may not support a wire element while the opposite walls' ends are open. The opposing wall surfaces carry a plurality of alternate vertical grooves and rod-like projections disposed in parallel and split horizontally by the fibrous membrane. The root of each projection includes a recessed portion in order to engage with the impression material and a handle attached to an outer wall of the pair outwardly extends anteriorly therefrom. A tongue retractor structure may be integrated on an inner wall of the pair.

12 Claims, 1 Drawing Sheet

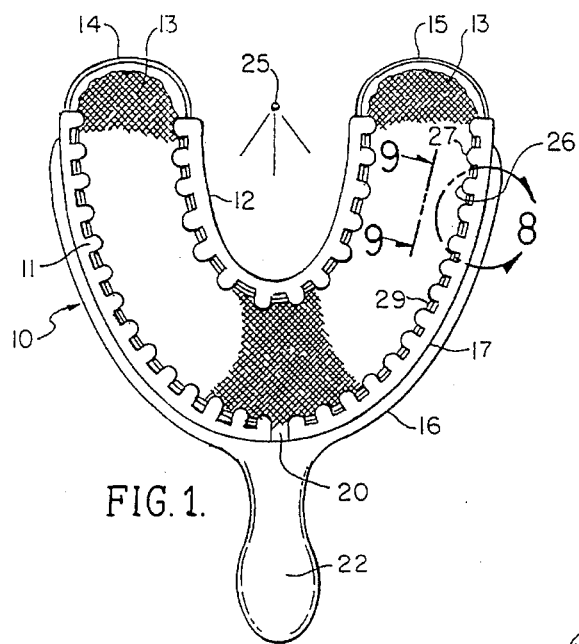
FIG. 1.
FIG. 3.
FIG. 4.
FIG. 5.
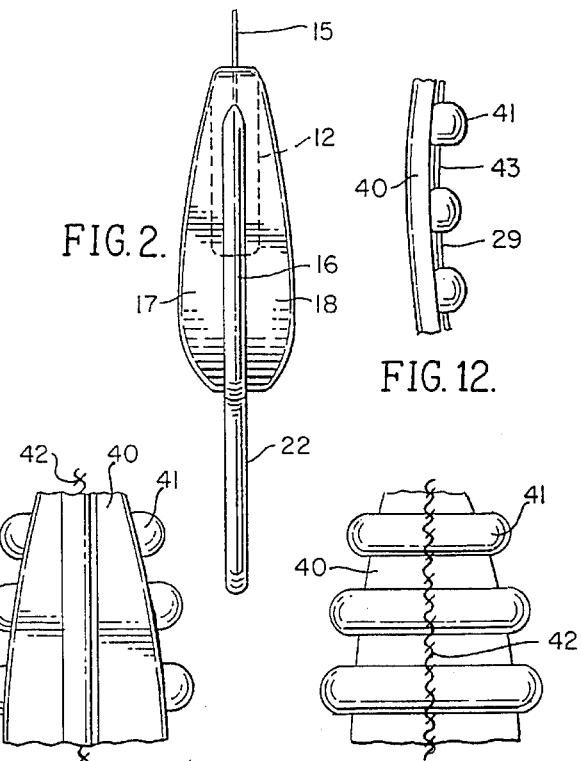
FIG. 2.
FIG. 10.
FIG. 11.
FIG. 12.
FIG. 6.
FIG. 7.
FIG. 8.
FIG. 9.

DENTAL IMPRESSION TRAY

Copending Application on which priority is claimed: Ser. No. 08-071,969, filed Jun. 7, 1993.

BACKGROUND OF THE INVENTION

1. Field of the Invention

The present invention relates to the field of dental instruments, and more particularly to a novel dental impression tray for obtaining an impression of a patient's dentition, including an impression of both the upper and lower arches and registering their relationship to each other in a single procedure.

2. Brief Description of the Prior Art

Prior or conventional impression trays are incapable of taking accurate impressions in a consistent manner. In general, dental trays for obtaining an impression of a patient's dentition include a tray portion contoured to fit within the patient's mouth so that when the patient closes or bites his teeth, an impression is made in the impression material. Initially, the tray is loaded with a suitable setting impression material on both hemispheres of the tray and situated opposite to the desired dentition part whereupon the patient bites into the impression material to form an impression of the dentition in the material. After the impression material sets, it is used as a mold into which plaster or the like can be poured which, upon setting, forms a model of the dentition.

Prior attempts have been made to solve a variety of problems in the use of dental impression trays and one such attempt is disclosed in U.S. Pat. No. 4,689,010. However, problems and difficulties have been encountered which stem largely from the fact that it is difficult to retain the impression material in place during and particularly after the impression bite has been made. At times, the supporting layer for the impression material may be perforated by the sharp teeth of the patient during the taking of the impression. Also, conventional trays do not properly flex during the impression procedure. At the end of the procedure, the tray sometimes reverts to a previous configuration causing distortion of the impression.

Most conventional triple bite trays have experienced problems in the area of distortion. The process of taking the impression allows the impression material which is set within the tray on both sides of the gauze support at which time the patient bites into the unset impression material such as polyvinyl-siloxane and when the material is set or hardened, the impression tray along with the impression material will be removed from the mouth. It is at this point that the distortion occurs due to the memory found in the plastics or metals used in the construction of the tray. This memory found in the arches connecting the parallel walls is stronger than the memory found in the impression material. As the patient bites down into the impression, the tray flexes in a Buccal/Lingual direction, due to the strength of the muscle of mouth and the design of the walls. Upon removal of the impression and the tray, the memory that is present within the plastics and metals will flex back to the original position it was in prior to the impression being taken. The result is a distorted impression due to the fact that the memory of the impression material especially over the occlusal surfaces, which have exposed the gauze supports, is weaker than the memory of a plastic or metal retro molar arch. Wire allows flexing of the tray so that the memory of the impression material is stronger than that of the wire.

SUMMARY OF THE INVENTION

Accordingly, the above problems and difficulties are overcome by the present invention which provides a novel dental impression tray having a pair of arcuate walls arranged in fixed spaced-apart relationship so as to define a working area between its opposing surfaces. A support material, such as a plastic embedded fibrous layered sheet, extends between the opposing walls and separates the working area into an upper and lower section so as to support the impression material in both hemispheres of the tray in order that both upper and lower impressions can be taken during the same procedure. In one form of the invention, a wire connects the ends of the walls posteriorly. In another form of the invention, the tray may take the form of a quadrant impression while in another form, a full mouth impression can be taken. Also, a tongue suppressor may be included for the convenience of the user and which will assist in the procedure.

Therefore, it is among the primary objects of the present invention to provide a novel dental impression tray which will prevent and avoid distortion of the impression made in an impression material which may be due to the memory found in conventional plastics or metals.

Another object of the present invention is to provide a novel improved dental impression tray which includes anti-distortion means for maintaining the impression material in place so that it will not move or distort while the impression is being made or after the impression has been made when the tray has been removed from the patient's mouth.

A further object of the present invention is to provide a novel dental tray which will permit the taking of accurate impressions for both the upper and the lower arches simultaneously and which will register their relationship to each other in a single step which will allow the tray to flex or adapt to existing dentition.

Yet another object of the present invention is to provide a novel dental tray which includes a tongue retractor integrally incorporated into the tray for the convenience during the impression taking procedure.

Another object resides in the placement of a handle integrally formed on the dental tray which extends anteriorly in a straight manner and which is substantially normal to the wall of the tray on which it is integrally formed.

Still another object of the invention is to provide a dental tray having an outer wall of greater height than its associated inner wall in order that the over-all dimension of the tray is reduced for the convenience and comfort of the patient and the minimizing of unnecessary forces of the mouth on the tray itself.

Another object resides in providing an impression material retaining means which is exterior of the plurality of retaining ribs and does not require weakening of rib roots at their juncture with the wall on which they are carried.

An important object further resides in constructing the dental tray to permit flexing of the tray so that the memory of the impression material is stronger than that of the arch construction.

Still another object is to provide an improved impression material retention means for holding the material in position subsequent to an impression procedure.

BRIEF DESCRIPTION OF THE DRAWINGS

The features of the present invention which are believed to be novel are set forth with particularity in the appended claims. The present invention, both as to its organization and manner of operation, together with further objects and advantages thereof, may best be understood with reference to the following description, taken in connection with the accompanying drawings in which:

FIG. 1 is a top plan view of the novel dental impression tray incorporating the present invention;

FIG. 2 is a side elevational view of the dental tray shown in FIG. 1;

FIG. 3 is an end elevational view of the dental tray shown in FIG. 1;

FIG. 4 is a top plan view of another version of another dental tray incorporating the present invention;

FIG. 5 is an end elevational view of the dental tray version shown in FIG. 4;

FIG. 6 is a fragmentary plan view of another version of the dental tray incorporating a tongue retractor ;

FIG. 7 is a transverse cross-sectional view of the tongue retractor shown in FIG. 6 as taken in the direction of arrows 7—7 thereof;

FIG. 8 is a fragmentary top plan view greatly enlarged to illustrate the impression material retaining means associated with the opposing walls incorporated into the trays illustrated in FIGS. 1, 4 and 6;

FIG. 9 is an enlarged elevational view of a wall used in the versions of the present invention and, in particular, as taken in the direction of arrows 9—9 of FIG. 1 and FIGS. 10–12 are enlarged fragmentary views of another version for positive retention of impression material.

DESCRIPTION OF THE PREFERRED EMBODIMENT

Referring to FIG. 1, the novel dental impression tray of the present invention is illustrated in the general direction of arrow 10 which is adapted for use in obtaining an impression of the posterior or bicuspid and molar part of both the upper and lower dentitions. It is understood that other configurations for obtaining impressions for other areas of the dentition are within the scope of the present invention. The tray 10 includes a pair of arcuate walls referred to in FIG. 1 as an outer wall 11 and an inner wall 12. The inner and outer walls are arranged in fixed spaced-apart relationship so as to define a working area therebetween which is intended to be occupied by a settable impression material. The material does not form a part of the present invention. However, the material is supported on a thin plastic embedded fibrous sheet or membrane or a non-woven fabric material, indicated by numeral 13, which has its edge marginal regions attached to the opposing walls 11 and 12 midway between the top and bottom of the walls. The membrane 13 may take the form of a paper, a sheet of plastic encased by fibrous material, close mesh netting, gauze or other plastic or paper-like materials or both. However, it is to be understood that the material is of high strength-to-weight ratio so as to eliminate perforations of the membrane while a dental impression is being made. Also, it must be borne in mind that the membrane 13 supports impression material on opposite sides so that the impression of both upper and lower teeth arches can be taken. Also, it is to be understood that the posterior end of the walls 11 and 12 may be joined by wires 14 and 15 which allow movement of the walls during the taking of the impression and afterwards as the impression material is being cured or set, it will maintain the shape of the wire due to the stronger memory of the impression material over the wire which is weaker in memory. The material of the wires 14 and 15 is of a non-memoric material so that even if the wires are flexed during the impression-taking procedure, the walls will not return to their pre-impression orientation due to the lack of spring-back or any memoric distortion encountered by the wires.

FIGS. 2 and 3 clearly illustrate that the walls are sectioned by the membrane 13 and an outer frame rib 16 so that numeral 17 represents an upper wall while numeral 18 represents a lower wall. FIG. 2 also illustrates that the outer wall 11 in the upper section 17 includes a depression, identified by numeral 20, which is to accommodate the patient's upper frenum during the impression-taking procedure. A shallower indentation 21 is formed in the lower wall section 18 of wall 11 which is to accommodate the lower frenum of the patient during the impression procedure. Furthermore, an integral handle 22 is formed with the wall 11 and rib 16 that extends anteriorly normal to the wall at the point of attachment.

It is also to be noted in FIG. 1 that the arcuate walls 11 and 12 are arranged so that their inner surfaces are relatively in parallel alignment with respect to one another and that they would share a common radial center, such as indicated by numeral 25. Also, and of prime importance, it can be seen that the inner opposing surfaces of the walls 11 and 12 are provided with a plurality of ribs, such as ribs 26 and 27 that are arranged in spaced-apart parallel relationship and which are normal or perpendicular to the supporting membrane 13. A larger view of these ribs is illustrated in FIG. 8 so that it can be seen that the grooves separating the adjacent ribs, such as 26 and 27, define a recess, as indicated by numeral 30 and 31 at the base or juncture of each rib with their respective wall. Also, the recesses 30 and 31 terminate with a linear surface 32 wherein the adjacent recesses 30 and 31 and linear surface 32 provide a retaining or holding means in cooperation with a retaining element 29 for maintaining impression material in place during and subsequent to the taking of an impression. All of the respective spaces or grooves between adjacent ones of the ribs include the holding means retaining element and this includes all of the ribs integrally formed on walls 11 and 12 respectively. The element may be a wire, plastic strip or the like and extends across the gap or space between adjacent ones of the ribs exteriorly of the ribs.

The retaining or holding means further is illustrated in FIG. 9 wherein it can be seen that each of the respective ribs, such as ribs 26 and 27, include rounded ends, such as illustrated by numeral 33 for the upper end and numeral 34 at the lower end. The sides of the ribs are linear surfaces joining the upper and lower rounded ends. By such a retaining or holding means, the material is held in place and will not move during the impression-taking or during the impression material setup or curing procedure. No irritation or discomfort is experienced by the patient while biting into the impression since there are no sharp exposed corners or edges which the patient could encounter.

Referring now in detail to FIG. 4, another embodiment of the invention is shown which represents one-half of the full tray shown in FIG. 1. The construction is identical with the exception that the wire 14 joining the ends of the walls 11 and 12 in FIG. 1 is not used and the tray construction is very flexible so that the impression material will hold the impressed bite without subsequent return to original shape. The membrane 13 supports both the walls 11 and 12. Furthermore, when the impression material has been placed in the work area on both sides of the membrane, additional support is given so that the impression procedure can be achieved. It is to be noted that the ribs and retainer elements, such as ribs 26 and 27, are identical to those shown in FIGS. 8 and 9. It also is to be noted that a wire could be used with the quadrant impression.

Referring now in detail to FIGS. 6 and 7, a tongue retractor is illustrated in another version of the invention wherein the retractor is identified by numeral 35 and is integrated with and as a part of the center wall 12, such as in the embodiment shown in FIG. 1. The retractor includes forward walls defining a hollow area identified by numeral 36 and the patient's tongue may be inserted into the hollow 36 between the walls to function as a retractor Impression material retention ribs and elements are employed as in the other versions.

FIGS. 10–12 illustrate a wall construction 40 for the tray which has a height lower than the height of the plurality of ribs 41. The sheet or membrane is indicated by numeral 42. By employing a wall height shorter than the ribs, impression material will be displaced not only between the ribs and about wire 43 but will reside over the edge of the wall and about the upper and lower portions of each rib. The narrow dimension of the wall compared to the length or height of the ribs permits the impression material to progress around and behind the ribs. This construction provides increased impression material retention.

In view of the foregoing, it can be seen that the novel dental impression tray of the present invention provides a retaining and holding means for the impression material which ensures that the material will not move either during the procedure in which an impression is being taken or subsequent to the procedure. Also, there is no discomfort to the patient because of the holding means and distortion is eliminated through the use of wire and other construction materials having non-memoric characteristics or the elimination of the wire altogether.

While particular embodiments of the present invention have been shown and described, it will be obvious to those skilled in the art that changes and modifications may be made without departing from this invention in its broader aspects and, therefore, the aim in the appended claims is to cover all such changes and modifications as fall within the true spirit and scope of this invention.

What is claimed is:

1. A dental impression tray comprising:

a pair of arcuate walls arranged in parallel spaced-apart relationship defining a working area between opposing wall surfaces and each wall of said pair having opposite ends;

a connection member of non-memoric characteristics connected between said wall ends of said pair of walls;

an impression material support membrane disposed in said working area and having opposite edge marginal regions attached to said pair of walls so as to divide said working area into an upper section and a lower section;

impression material retaining means carried on said wall opposing surfaces;

said retaining means comprising a plurality of ribs integral with each of said opposing wall surfaces respectively.

2. The invention as defined in claim 1 wherein;

said connection member is disposed between said pair of walls at each end respectively allowing said walls to move independently of each other so as to not revert back to an original position.

3. The invention as defined in claim 1 wherein;

said support membrane includes a sheet of plastic encased by a fibrous material on opposite sides of said plastic sheet.

4. A dental impression tray comprising:

a pair of arcuate walls arranged in parallel spaced-apart relationship defining a working area between opposing wall surfaces and each wall of said pair having opposite ends;

an impression material support membrane disposed in said working area and having opposite edge marginal regions attached to said pair of walls so as to divide said working area into an upper section and a lower section;

impression material retaining means carried on said wall opposing surfaces;

said retaining means comprising a plurality of ribs integral with each of said opposing wall surfaces respectively;

said pair of walls are of a given dimensional height defined between upper and lower edges thereof; and said ribs having a dimensional height greater than said dimensional height of said walls so as to extend beyond said wall upper and lower edges.

5. A dental impression tray comprising:

a pair of arcuate walls arranged in parallel spaced-apart relationship defining a working area between opposing wall surfaces and each wall of said pair having opposite ends;

an impression material support membrane disposed in said working area and having opposite edge marginal regions attached to said pair of walls so as to divide said working area into an upper section and a lower section;

impression material retaining means carried on said wall opposing surfaces;

said retaining means comprising a plurality of ribs integral with each of said opposing wall surfaces respectively; and said support membrane includes a sheet of plastic including by a fibrous material on opposite sides of said plastic sheet.

6. The invention as defined in claim 5 wherein:

said support membrane is a sheet of plastic embedded with fibrous material.

7. The invention as defined in claim 5 wherein:

said fibrous material is a gauze medium embedded with a plastic-like material.

8. A dental impression tray providing comfort to the patient and that is non-injurious comprising:

a pair of arcuate walls arranged in parallel spaced-apart relationship defining a work area between opposing wall surfaces;

an impression material support membrane disposed across said work area and having opposite edge marginal regions attached to said pair of walls so as to divide said work area into an upper section and a lower section;

impression material retaining means carried on the opposing wall surfaces of said pair of walls comprising a plurality of spaced-apart ribs integrally formed with each of said walls respectively;

said pair of walls include opposite ends defining open ends of said work area respectively in spaced-apart relationship; and said retaining means further includes a wire extending through said plurality of ribs engageable with said impression material.

9. A dental impression tray providing comfort to the patient and that is non-injurious comprising:
- a pair of arcuate walls arranged in parallel spaced-apart relationship defining a work area between opposing wall surfaces;
- an impression material support membrane disposed across said work area and having opposite edge marginal regions attached to said pair of walls so as to divide said work area into an upper section and a lower section;
- impression material retaining means carried on the opposing wall surfaces of said pair of walls comprising a plurality of spaced-apart elongated ribs integrally formed with each of said walls respectively;
- said pair of walls include opposite ends defining open ends of said work area respectively in spaced-apart relationship constituting a rear end disposed at the rear of a patient's mouth with its opposite end constituting a front end;
- said pair of walls are of a given dimensional height defined between upper and lower edges thereof; and
- said ribs having a dimensional height greater than said dimensional height of said walls so as to extend beyond said wall upper and lower edges.

10. A dental impression tray providing comfort to the patient and that is non-injurious comprising;
- a pair of arcuate walls arranged in parallel spaced-apart relationship defining a work area between opposing wall surfaces;
- an impression material support membrane disposed across said work area and having opposite edge marginal regions attached to said pair of walls so as to divide said work area into an upper section and a lower section;
- impression material retaining means carried on the opposing wall surfaces of said pair of walls comprising a plurality of spaced-apart elongated ribs integrally formed with each of said walls respectively;
- said pair of walls include opposite ends defining open ends of said work area respectively in spaced-apart relationship constituting a rear end disposed at the rear of a patient's mouth with its opposite end constituting a front end; and
- a metal member having its opposite ends attached to said wall ends constituting said rear end in spaced-apart relationship to said support membrane.

11. A dental impression tray providing comfort to the patient and that is non-injurious comprising;
- a pair of arcuate walls arranged in parallel spaced-apart relationship defining a work area between opposing wall surfaces;
- an impression material support membrane disposed across said work area and having opposite edge marginal regions attached to said pair of walls so as to divide said work area into an upper section and a lower section;
- impression material retaining means carried on the opposing wall surfaces of said pair of walls comprising a plurality of spaced-apart elongated ribs integrally formed with each of said walls respectively;
- said pair of walls include opposite ends defining open ends of said work area respectively in spaced-apart relationship constituting a rear end disposed at the rear of a patient's mouth with its opposite end constituting a front end;
- said pair of walls are of a given dimensional height defined between upper and lower edges thereof; and
- said ribs having a dimensional height greater than said dimensional height of said walls so as to extend beyond said wall upper and lower edges.

12. A dental impression tray providing comfort to the patient and that is non-injurious comprising;
- a pair of arcuate walls arranged in parallel spaced-apart relationship defining a work area between opposing wall surfaces;
- an impression material support membrane disposed across said work area and having opposite edge marginal regions attached to said pair of walls so as to divide said work area into an upper section and a lower section;
- impression material retaining means carried on the opposing wall surfaces of said pair of walls comprising a plurality of spaced-apart elongated ribs integrally formed with each of said walls respectively;
- said pair of walls include opposite ends defining open ends of said work area respectively in spaced-apart relationship constituting a rear end disposed at the rear of a patient's mouth with its opposite end constituting a front end; and
- said retaining means further includes a wire extending through said plurality of ribs engageable with said impression material.

* * * * *